United States Patent [19]

Siczek et al.

[11] Patent Number: 5,515,416
[45] Date of Patent: May 7, 1996

[54] BI-PLANE IMAGING DEVICE

[76] Inventors: Bernard W. Siczek, 1252 Chinook Way, Boulder, Colo. 80303-1411; Roman W. Siczek, 2399 Gross Lake Rd., Lindenhurst, Ill. 60046

[21] Appl. No.: 453,170
[22] Filed: May 30, 1995
[51] Int. Cl.$^6$ ........................................ H05G 1/02
[52] U.S. Cl. ........................... 378/197; 378/196
[58] Field of Search ........................ 378/195–198

[56] References Cited

U.S. PATENT DOCUMENTS 3,549,885  12/1970  Andersson ........................ 378/197
4,541,293  9/1985  Caugant et al. ........................ 378/197

Primary Examiner—Craig E. Church

[57] ABSTRACT

This invention relates to a bi-plane X-ray imaging medical system having two radiation axis with a common isocenter for simultaneous viewing of a targeted object in two planes for three dimensional orientation, these two radiation axes can be rotated about the isocenter, thus rotating these two planes individually or simultaneously and varying the angle between them for most advantageous imaging. And further, varying the angle allows for larger opening for access to the patient during a surgery or for loading/unloading the patient.

8 Claims, 5 Drawing Sheets

BI-PLANE IMAGING DEVICE

BACKGROUND OF INVENTION

1. Field of Invention

The present invention relates to a field of medical instrumentation used for fluoroscopic and radiographic imaging of a body from a multiplicity of viewpoints simultaneously in two distinct planes, at a varying angle. The invention is useful for cardiac and electro-physiological imaging, for bone, abdominal and neuro-surgical applications.

2. Prior Art

The diagnostic bi-plane imaging system for viewing of a targeted object within a body simultaneously in two planes for three dimensional orientation is well known.

In the prior art, for example in the cardiac application, the bi-plane imaging system includes a first C- or U-arm mounted on the floor for imaging in the first plane and a second C-arm mounted on the ceiling for imaging in the second plane, thus providing flexibility of the relative positioning of the imaging planes, which planes do not necessarily have a common isocenter. A disadvantage of this system is a limited access to the patient, high cost of installation of the rails on the ceiling and lack of sterile environment due to the ceiling rails.

Another known bi-plane imaging system includes a G like structure limited to two orthogonal planes of imaging only that is insufficient in many examinations and very restricted access to the patient.

Still another known configuration is an O-ring like, providing even less access to the patient, used mostly for the head examination.

SUMMARY OF INVENTION

The present invention relates to a bi-plane X-ray imaging system allowing for three dimensional orientation of a targeted object within a body by simultaneously viewing the object in two planes, not necessarily orthogonal to one another.

The biplane imaging system according to this invention comprises of two C-arms, each having an X-ray source and receptor mounted thereon; wherein these arms are mounted on a carriage and can move relative to each other either in a telescopic arrangement or side-by-side parallely so that the two planes of viewing are at a variety of angles. A large angle providing a large opening sufficient for loading or unloading a patient from a side and a good access to the patient. The carriage is rotationally mounted on a floor plate for rotation about a vertical axis passing through the isocenter of the radiation axes for additional flexibility of positioning.

Further, in some surgical applications it is desirable to move the imaging apparatus away from the operation table sideways; for this reason the apparatus can be put on wheels. Alternatively, the C-arms can be mounted on a surgical pivotal arm extending from a ceiling (such as used in the X-ray surgical equipment) or from a corner stand, voiding rails to allow for sterile environment.

The bi-plane imaging system being isocentric can accept the orbital aiming device as described in U.S. Pat. No. 5,129,911.

DETAILED DESCRIPTION OF THE PRESENTLY PREFERRED EMBODIMENT

Figure 1:
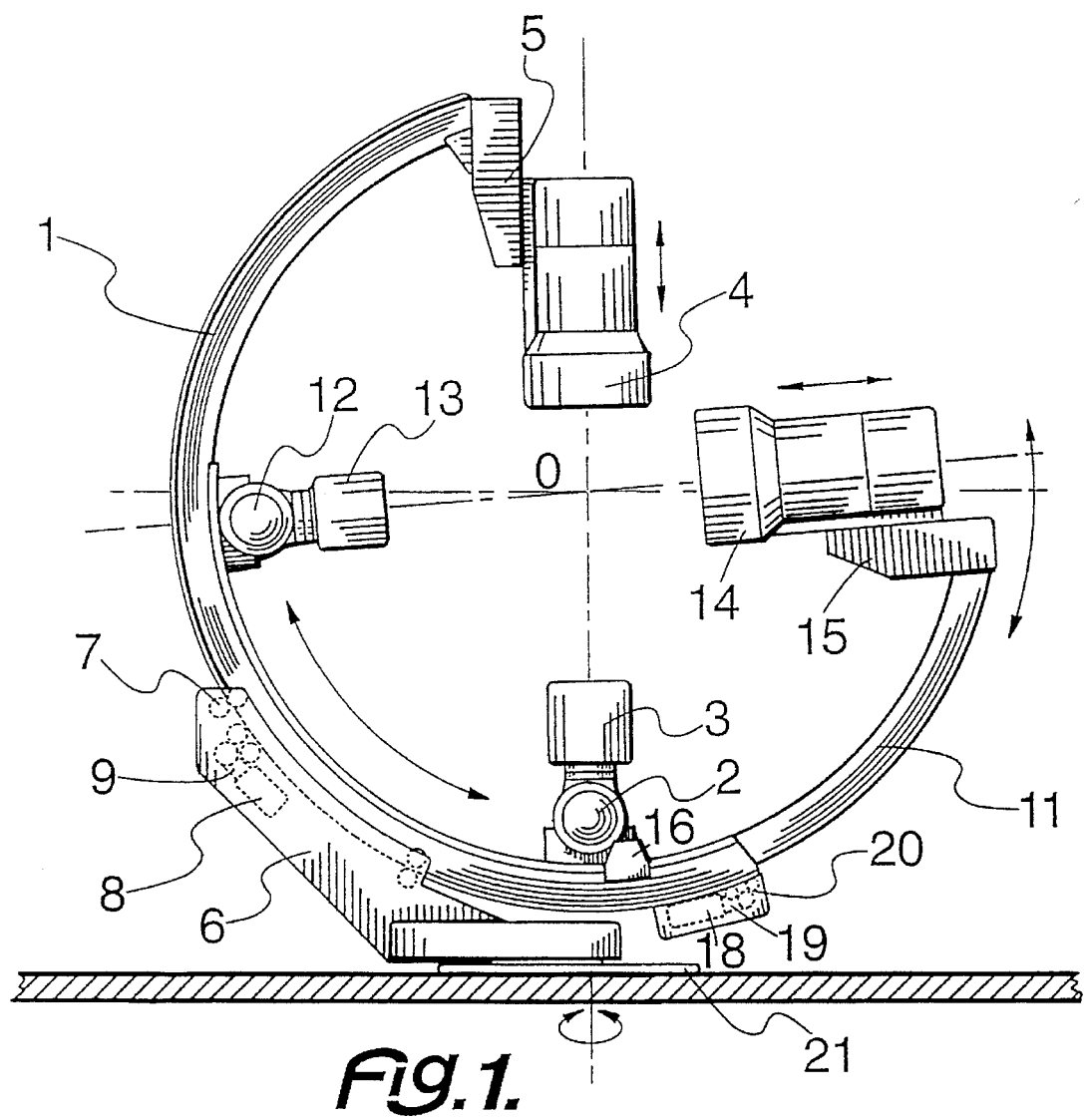
FIG. 1 is a side view of the bi-plane imaging system according to present invention, wherein the imaging planes are at less than a 90° angle approximately.
Figure 2:
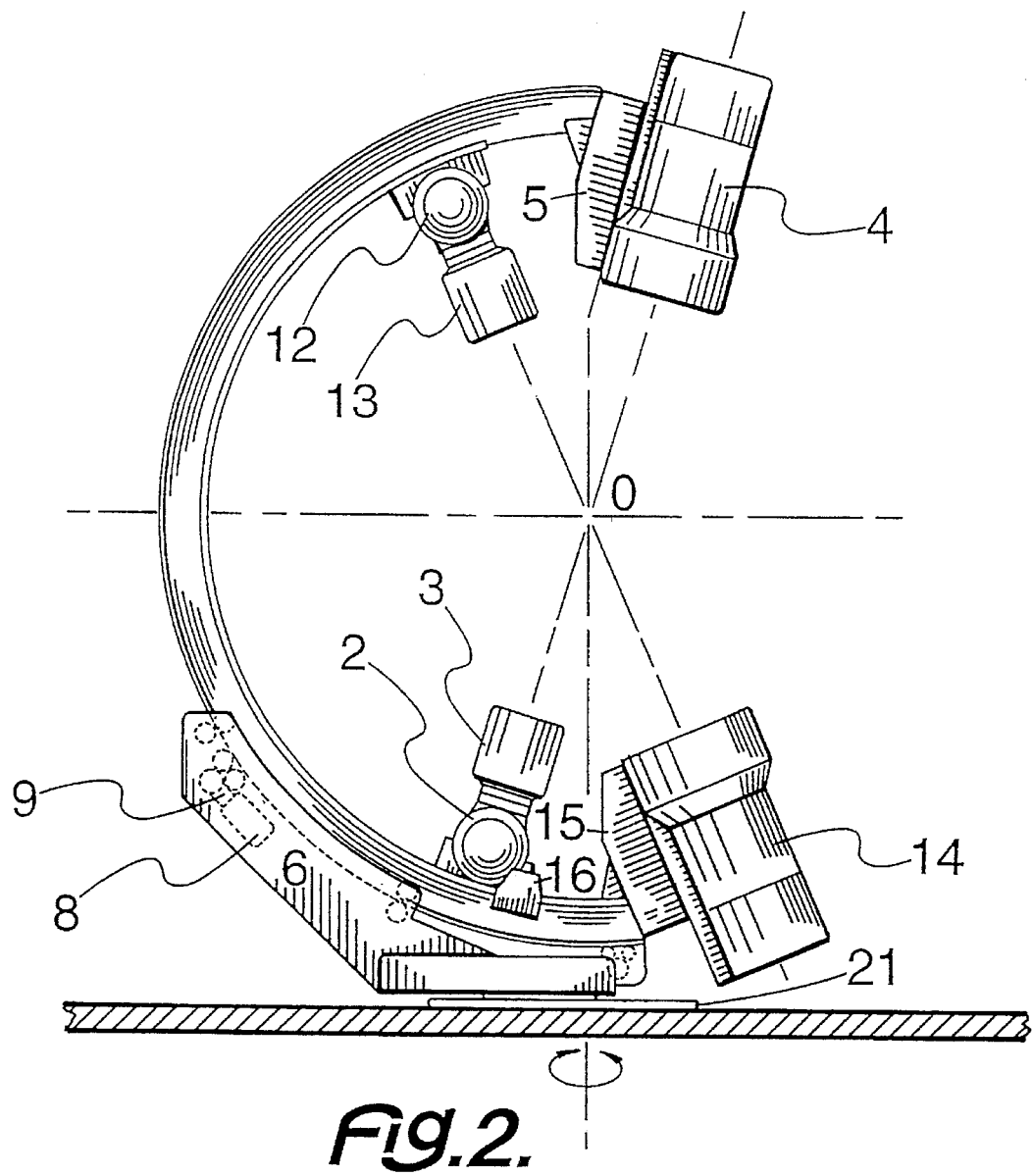
FIG. 2 is the same side view of the bi-plane imaging system as in FIG. 1, wherein the imaging planes are at a large angle to provide the biggest opening.
Figure 3:
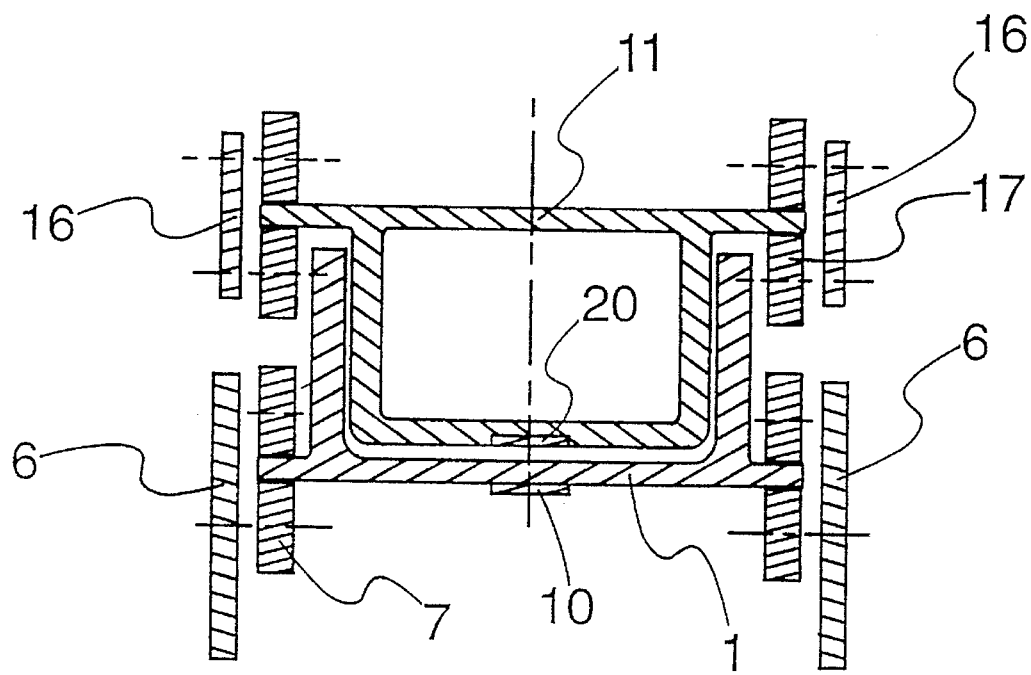
FIG. 3 illustrates a cross section of an embodiment wherein one C-arm is placed within the other C-arm for telescopic movement therebetween.

Referring to FIGS. 1, 2 and 3 the bi-plane X-ray imaging system is shown comprising a C-arm 1 carrying an X-ray source 2, a collimator 3 and an image receptor 4 mounted on a slide 5; the C-arm rotatably mounted on a carriage 6 having bearings 7 and driven by means of a motor 8 with a reducer 9 and a timing belt 10.

Further comprising, a C-arm 11 carrying an X-ray source 12, a collimator 13 and an image receptor 14 movably mounted on a slide 15 for varying its distance to an isocenter O. C-arm 11 is movably mounted on a carriage 16 having bearings 17, which carriage 16 is slidably mounted on C-arm 1. C-arm 11 moves relative to C-arm 1 driven by means of a motor 18, a reducer 19 and a timing belt 20.

FIG. 3 illustrates a cross section of C-arm 11 mounted in a telescopic arrangement on C-arm 1, wherein x-ray source 2 and a collimator 3 are attached to an outside perimeter of C-arm 1 so that C-arm 11 can move along an inside perimeter of C-arm 1.

Figure 4:
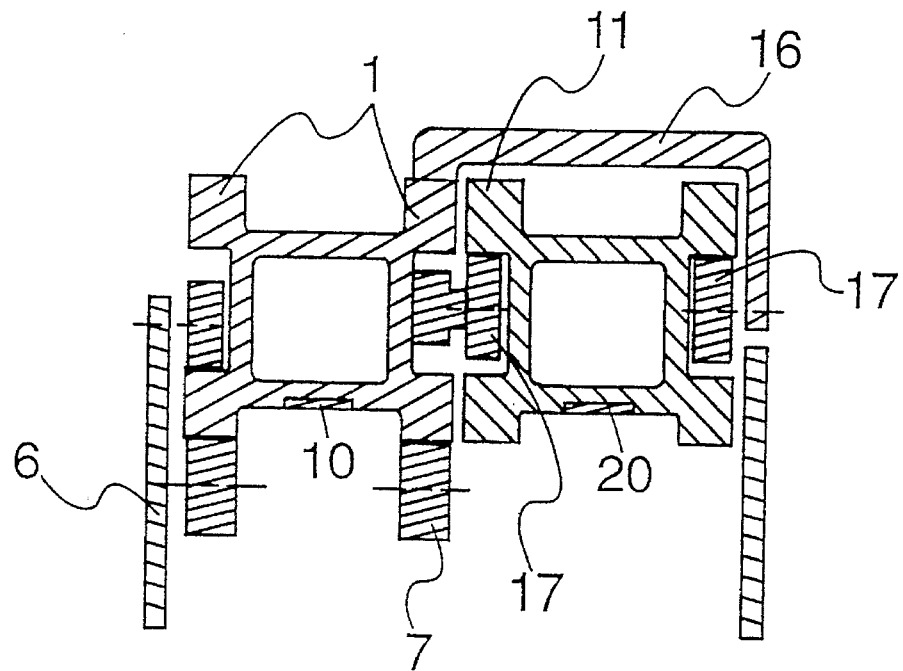
FIG. 4 illustrates a cross section of an alternative embodiment, wherein the C-arms are placed side by side.

FIG. 4 illustrates an alternative relative configuration of C-arm 1 and C-arm 11, wherein C-arm 11 is slidably mounted on a side of C-arm 1.

In both of the above configuration the movement of the C-arms together or relative to each other is the same, and is illustrated in FIG. 1 and FIG. 2. C-arm 1 can be rotated in carriage 6 so that both C-arms are rotated simultaneously about the isocenter O without their relative displacement.

Also shown in FIG. 1 and 2 is carriage 6 mounted on bearings attached to a floor plate 21 so that C-arm 1 with carriage 6 can be rotated about a vertical axis passing through the isocenter O.

Figure 5:
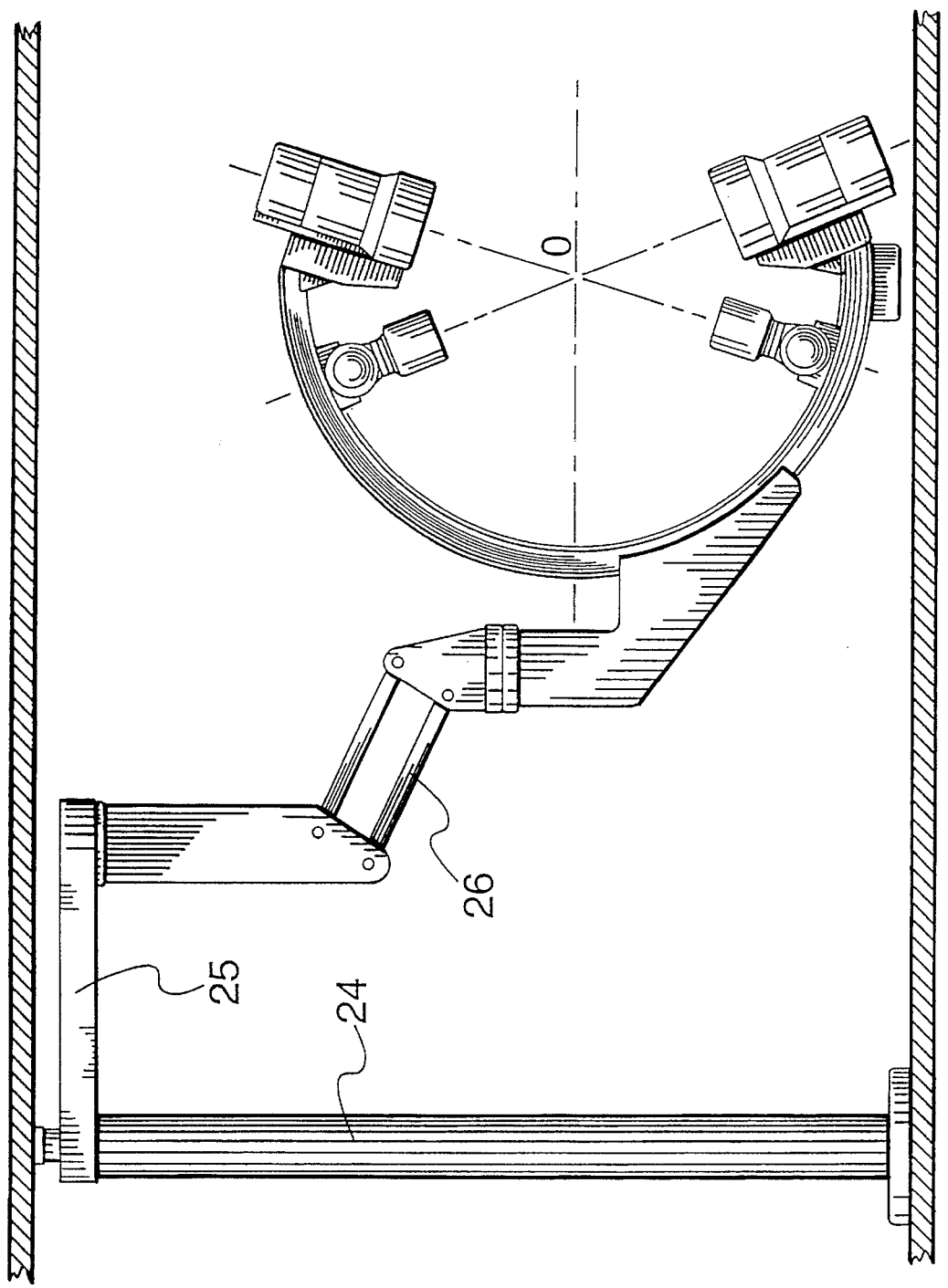
FIG. 5 illustrates the bi-plane imaging system mounted on a floor-ceiling stand.

FIG. 5 shows the bi-plane imaging device mounted on a floor-ceiling stand 24 with a pivotal arm 25 and a pantographic arm 26.

Figure 6:
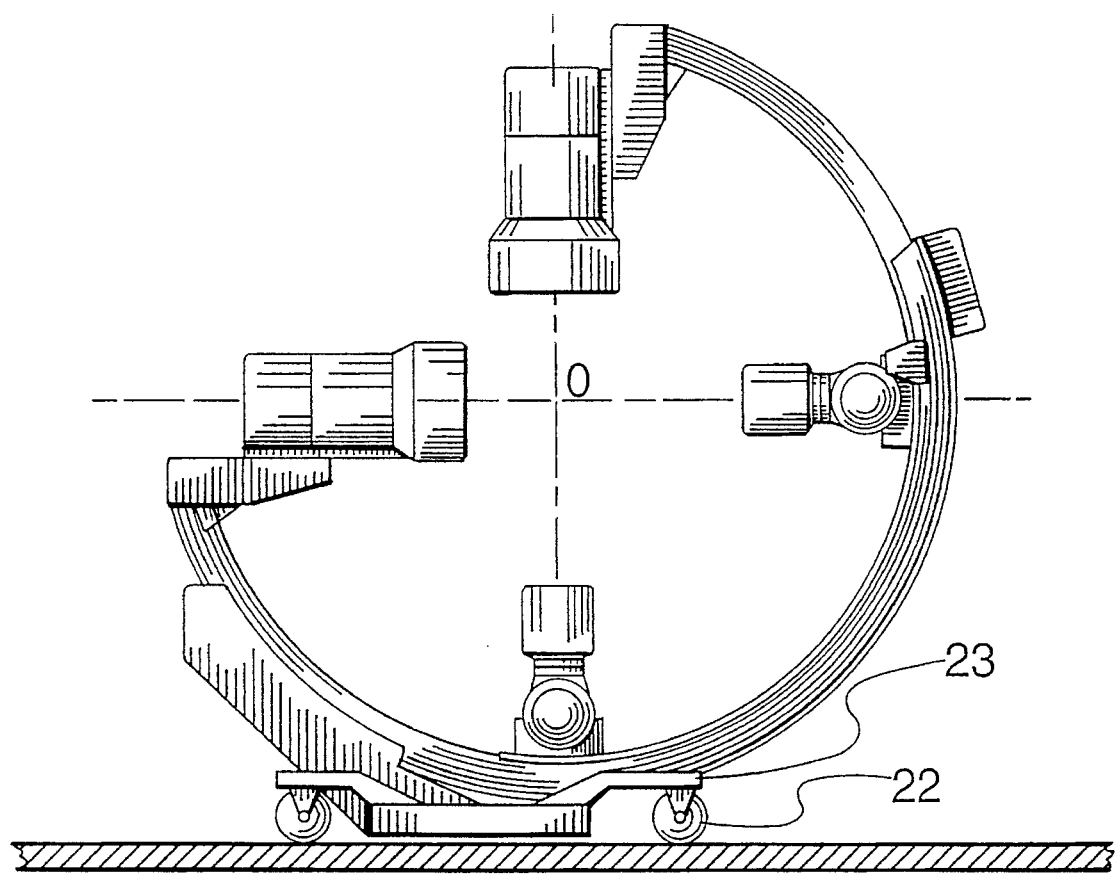
FIG. 6 illustrates the by plane imaging system mounted on wheels for mobility.

FIG. 6 shows the bi-plane imaging device mounted on a plate 23 supported by casters 22.

We claim:

1. A bi-plane x-ray imaging system for viewing a targeted object within a body simultaneously in two planes for three dimensional orientation comprising two C-arms, each of the two arms carrying an x-ray tube and an X-ray image receptor defining an radiation axis, wherein these radiation axes have a common isocenter, and wherein these two planes can be rotated individually about the isocenter for varying an angle between said two imaging planes and wherein said C-arms can be rotated simultaneously about said isocenter, and further, wherein said C-arms are coupled in sliding telescopic engagement, said two arms supported on a carriage.

2. A bi-plane x-ray imaging system for viewing a targeted object within a body simultaneously in two planes for three dimensional orientation comprising two C-arms, each of the two arms carrying an x-ray tube and an X-ray image receptor defining an radiation axis, wherein these radiation axes have a common isocenter, and wherein these two planes can be rotated individually about the isocenter for varying an angle between said two imaging planes and wherein said C-arms can be rotated simultaneously about said isocenter, and further, wherein said C-arms are coupled in sliding parallel engagement on a carriage.

3. The bi-plane X-ray imaging apparatus as in claim 1, coupled to a data acquiring device to create a stereo view.

4. The bi-plane X-ray imaging apparatus as in claim 2, coupled to a data acquiring device to create a stereo view.

5. The bi-plane x-ray imaging apparatus as in claim 1, wherein said apparatus is on wheels.

6. The bi-plane x-ray imaging apparatus as in claim 2, wherein said apparatus is on wheels.

7. The bi-plane x-ray imaging apparatus as in claim 1, wherein said apparatus is suspended on pivotal arms in proximity to a ceiling.

8. The bi-plane x-ray imaging apparatus as in claim 2, wherein said apparatus is suspended on pivotal arms in proximity to a ceiling.

* * * * *